United States Patent [19]

Fukui et al.

[11] Patent Number: 4,602,007

[45] Date of Patent: Jul. 22, 1986

[54] SALICYLATE CULTURE MEDIA FOR INACTIVATION OF BACTERIAL GROWTH INHIBITORS

[75] Inventors: George M. Fukui; Herbert J. Spencer; Laurens R. Williams, II, all of Irving, Tex.

[73] Assignee: Abbott Laboratories, North Chicago, Ill.

[21] Appl. No.: 651,136

[22] Filed: Nov. 5, 1984

Related U.S. Application Data

[62] Division of Ser. No. 373,829, May 3, 1982, Pat. No. 4,483,926, which is a division of Ser. No. 147,794, May 8, 1980, Pat. No. 4,340,679.

[51] Int. Cl.$^4$ ................................................ C12Q 1/18
[52] U.S. Cl. ....................................... 514/159; 435/32
[58] Field of Search .................... 435/32, 34, 39, 253; 436/175; 514/159, 165

[56] References Cited

U.S. PATENT DOCUMENTS

| | | | |
|---|---|---|---|
| 3,671,399 | 6/1972 | Cekoric et al. | 435/253 |
| 4,340,679 | 7/1982 | Fukui et al. | 435/253 |
| 4,483,926 | 11/1984 | Fukui et al. | 435/34 |

*Primary Examiner*—Hiram H. Bernstein
*Attorney, Agent, or Firm*—James L. Wilcox

[57] ABSTRACT

This invention encompasses methods and reagents for inactivation of bacterial growth inhibitors present in blood, serum or plasma. It has been found that salicylates and closely related compounds will neutralize bacterial growth inhibitors present in the blood of many patients. The addition of salicylate to conventional growth medium also provides a reagent for monitoring the antibiotic levels in blood by enabling measurement of the effect of the antibiotic against a standard test organism without interference from the bacterial growth inhibitor present in sera.

1 Claim, No Drawings

SALICYLATE CULTURE MEDIA FOR INACTIVATION OF BACTERIAL GROWTH INHIBITORS

This is a division of application Ser. No. 373,829, filed May 3, 1982, now U.S. Pat. No. 4,483,926; which is a divisional of U.S. Ser. No. 147,794, filed May 8, 1980, now U.S. Pat No. 4,340,679, issued July 20, 1982.

BACKGROUND OF THE INVENTION

It has been found that blood and blood components such as plasma and serum of both normal adults and of patients who have been administered antibiotics contain nonspecific bacteriostatic substance, i.e., bacterial growth inhibitor. This observation was made while conducting studies relating to an automated serum bioassay for drugs such as gentamicin, tobramycin, or amikacin in blood serum or plasma.

Typically, serum samples are assayed using a bacterial culture in growth medium, and the ability of the patient serum to inhibit bacterial growth is a measure of the level of antibiotic content in the serum specimen. It was unexpectedly found that about 50% of the human sera tested contained nonspecific bacterial growth inhibitor which caused the serum to give erratic bioassay results. In other words, bacterial growth could be inhibited irrespective of the antibiotic levels present in the serum or plasma being tested. It has been discovered that salicylates and closely related compounds will neutralize or inactivate these bacterial growth inhibitors present in blood or blood components.

BRIEF SUMMARY OF THE INVENTION

This invention encompasses methods and reagents for inactivation or neutralization of bacterial growth inhibitor present in blood, serum or plasma. It has been found that salicylates and closely related compounds will neutralize such substances in specimens from both normal subjects and from patients who have received antibiotic. Thus, the addition of salicylate or structurally related compounds to culture medium used to culture bacteria in the presence of blood or blood components (serum, plasma) provides an effective method for neutralizing such bacterial growth inhibitor present in blood plasma or serum. Culture media containing an amount of bacterial growth inhibitor neutralizing agent to effectively neutralize such bacterial growth inhibitors is a reagent of the invention. A preferred reagent is culture media containing sodium salicylate or acetyl salicylate acid.

DETAILED DESCRIPTION OF THE INVENTION

Those skilled in the microbiological arts will recognize the equivalency of simple halo (chloro, fluoro, and bromo) ring substituted derivatives of these compounds, as well as lower alkyl ring substituted derivatives.

Typical salicylates are listed in the Merck Index, 9th Edition, Merck & Company, Inc., Rahway, N.J., USA, pages 1078-1081.

Acetylsalicylic acid and salicylate salts such as sodium and potassium salicylate are preferred salicylates. Concentrations of about 5 to 15 millimolar are preferred, with 8-15 millimolar being further preferred, and 10 millimolar of sodium salicylate being a most preferred effective amount of salicylate to neutralize bacterial growth-inhibiting substances in the blood or serum, but not so concentrated as to inhibit the growth of the bacteria per se.

Sodium gentisate and resorcinol have also been found to be useful in practicing this invention.

A preferred growth medium for serum bioassay experiments is as follows:

| Mueller-Hinton Broth | Grams/Liter |
|---|---|
| Beef, Infusion | 30.0 |
| Casamino Acids | 17.5 |
| Soluble Starch | 1.5 |
| Sodium Salicylate | 1.6 |

Dissolve above in one liter of deionized water, adjust pH to 8.5 with addition of sodium hydroxide and sterilize in autoclave at 15 pounds pressure, 121° C., for twenty minutes.

Trypticase soy broth and brain-heart infusion, and the like, are other suitable media.

By salicylate is meant salicylic acid, biologically compatible salts thereof, esters and amide derivatives thereof, closely related compounds such as benzoic acid and biologically acceptable acid addition salts thereof, and related hydroxylated benzoic acid derivatives are operative in this invention. The term salicylate especially includes chemical compounds which hydrolyze to the salicylate ion in aqueous solution.

Compounds of the following structures have been found active at 10 millimolar concentration.

TABLE I
RELATIVE ACTIVITY OF SALICYLATE ANALOGS IN NEUTRALIZATION OF BACTERIOSTATIC SUBSTANCES(S) IN HUMAN BLOOD SERA

| Compound | Molecular Structure | Activity (@ 10 mM) |
|---|---|---|
| Acetyl Salicylate (sodium salt) | COONa, OCOCH₃ (benzene ring) | + |
| Sodium Salicylate | COONa, OH (benzene ring) | + |
| Salicylamide | COONH₂, OH (benzene ring) | + |
| Sodium Gentisate | COONa, OH, HO (benzene ring) | + |
| Resorcinol | OH, OH (benzene ring) | + |
| Benzoic Acid | COOH (benzene ring) | + |

Those skilled in the bacteriological arts will recognize a wide variety of growth media to which salicylates can be added for practicing this invention.

This serum bioassay for gentamicin and amikacin is performed by adding 25 microliters of serum or squeous reference stand of the antibiotic to specific cuvetts in duplicate. For tobramycin assay, fifty microliters of serum or reference standard are added to the cuvettes. Each assay contains 3 levels of reference standards in duplicate and a culture control with no added antibiotic.

Two hundred microliters of an 0.5 McFarland standard suspension in 0.85% sodium chloride solution, prepared from a fresh blood agar plate culture of *Klebsiella pneumoniae*, ATCC 27799, is used for the assay. The bioassay is performed in an MS-2 instrument sold by Abbott Laboratories, North Chicago, Ill., of the type described in U.S. Pat. Nos. 3,847,745; 3,837,746; Re. 28,800, and Re. 28,801. Inhibition of the assay organism can be monitored in other conventional spectrophotometers. Transfer of inoculum in the MS-2 instrument is performed when bacterial growth in the upper chamber reaches an optical density of 0.008 with a light source of 675 nM (light-emitting diode, LED). The assay is permitted to run for a minimum of 4 hours at 35° C. for analysis of antibiotic concentration in the blood serum specimen(s) being tested.

In a similar manner culturing bacteria in blood or blood products is facilitated by the addition of bacterial growth inhibitor neutralizing agents such as a salicylate to the culture media. Culturing of blood samples is widely used in hospitals and laboratories to the existance of infection and to isolate the infecting organism.

What is claimed is:

1. A method for treating blood or blood components containing bacteria, which method comprises adding to the blood or blood component an amount of a salicylate effective to neutralize naturally occurring bacterial growth inhibitor.

* * * * *